United States Patent
Honda et al.

(10) Patent No.: US 11,506,612 B2
(45) Date of Patent: Nov. 22, 2022

(54) SURFACE ENHANCED RAMAN SPECTROSCOPY POINT OF CARE VIRUS DETECTION SYSTEM

(71) Applicant: TH Bioventures, LLC, Memphis, TN (US)

(72) Inventors: Leif E. Honda, Rye, NH (US); Phil A Cestaro, Memphis, TN (US); Jon C Wetzel, Germantown, TN (US); Songhao Li, Brighton, MA (US); Arsen Hajian, Brookline, MA (US); Ronald J Sostek, Waltham, MA (US)

(73) Assignee: TH Bioventures, LLC, Memphis, TN (US)

(*) Notice: Subject to any disclaimer, the term of this patent is extended or adjusted under 35 U.S.C. 154(b) by 0 days.

(21) Appl. No.: 17/389,292

(22) Filed: Jul. 29, 2021

(65) Prior Publication Data
US 2022/0034816 A1 Feb. 3, 2022

Related U.S. Application Data (60) Provisional application No. 63/058,180, filed on Jul. 29, 2020.

(51) Int. Cl.
*G01J 3/44* (2006.01)
*G01N 21/65* (2006.01)
(Continued)

(52) U.S. Cl.
CPC .......... *G01N 21/658* (2013.01); *G01J 3/0275* (2013.01); *G01J 3/44* (2013.01);
(Continued)

(58) Field of Classification Search
CPC ........ G01J 3/44; G01N 21/658; G01N 33/569
See application file for complete search history.

(56) References Cited

U.S. PATENT DOCUMENTS 3,065,095 A1 11/2011 Rekenthaler et al.
8,767,217 B2 7/2014 Hajian et al.
(Continued)

FOREIGN PATENT DOCUMENTS

AU 2015202843 B2 7/2017
CA 2776233 A1 8/2011

OTHER PUBLICATIONS

Downes, "Wide area Raman Spectroscopy", Feb. 2019 (Year: 2019).*

(Continued)

*Primary Examiner* — Maurice C Smith
(74) *Attorney, Agent, or Firm* — Capitol City TechLaw, PLLC; Samuel P. Burkholder; Jasbir Singh (57) ABSTRACT

A system and method for detecting pathogenetic analytes including exciting a large target input area with radiation to produce scattered light to form an input beam, reformatting, with an optical slicer system, the input beam to produce an output beam, dispersing the output beam to produce an output area, capturing excitation data from the output area; and determining, with a processor, a presence of a particular analyte in the input area based on the excitation data. The input area can be greater than 100 micron squared and less than one million microns squared. The optical slicer system can be a high throughput virtual slit system. SERS analysis detects analytes of interest with both high resolution and sensitivity simultaneously, and is applicable for detection of the presence of viruses.

19 Claims, 7 Drawing Sheets

(51) Int. Cl.
    *G01J 3/02*     (2006.01)
    *G01N 33/569*     (2006.01)

(52) U.S. Cl.
    CPC . *G01N 33/56905* (2013.01); *G01N 33/56911* (2013.01); *G01N 33/56983* (2013.01); *G01N 2201/06113* (2013.01)

(56) References Cited

U.S. PATENT DOCUMENTS

| | | | |
|---|---|---|---|
| 8,937,723 | B2 | 1/2015 | Cenko et al. |
| 8,958,065 | B2 | 2/2015 | Meade et al. |
| 9,228,900 | B2 | 1/2016 | Preston et al. |
| 9,574,941 | B2 | 2/2017 | Nitkowski et al. |
| 2014/0349337 | A1* | 11/2014 | Dasari .................. G01N 21/65 435/40.5 |

OTHER PUBLICATIONS

Edward Gooding, "The High Throughput Virtual Slit enables compact, inexpensive Raman spectral imagers", 2018 (Year: 2018).*

Strola, "Raman microspectrometer combined with scattering microscopy and lensless imaging for bacteria Identification", SPIE 2013 (Year: 2013).*

Cheng Zong, "Transient Electrochemical Surface-Enhanced Raman Spectroscopy: A Millisecond Time-Resolved Study of an Electrochemical Redox Process", 2015 (Year: 2015).*

Johnson Materials Research Group, http://www.uwyo.edu/johnsonmaterials/research-projects/sers-biosensors.html, Jun. 6, 2018 (Year: 2018).*

Jeffrey T. Meade, "Simultaneous High-Resolution and High-Throughput Spectrometer Design Based on Virtual Slit Technology", 2012 Optical Society of America (Year: 2012).*

EPO, International Search Report dated Nov. 8, 2021, in PCT application No. PCT/US2021/071059.

Gooding, Edward, et al., "Fast, Cheap and In Control: Spectral Imaging with Handheld Devices," Proceedings of SPIE, May 5, 2017, pp. 102100E1-102100E7, vol. 10210, Bellingham, WA, US.

Gooding, Edward, et al., "The High Throughput Virtual Slit enables compact, inexpensive Raman spectral imagers,"Progress in Biomedical Optics and Imaging, SPIE—International Society for Optical Engineering, Feb. 13, 2018, pp. 104900T1-104900T8, vol. 10490, Bellingham, WA, US.

Hajian, Arsen, et al., "Powerful DMD-based light sources with a high throughput virtual slit," Proceedings of SPIE, Feb. 13, 2016, pp. 97610E1-97610E4, vol. 9761, Bellingham, WA, US.

Khan, S., et al., "Evaluation of Raman spectroscopy in comparison to commonly performed dengue diagnostic tests," Journal of Biomedical Optics, vol. 21, No. 9, p. 095005, Sep. 2016, SPIE, doi: 10.1117/1.JBO.21.9.095005.

Marks, H., et al., "Surface enhanced Raman spectroscopy (SERS) for in vitro diagnostic testing at the point of care," Nanophotonics, vol. 6, No. 4, pp. 681-701, 2017, DOI 10.1515/nanoph-2016-0180, De Gruyter.

Moor K., et al., "Noninvasive and label-free determination of virus infected cells by Raman spectroscopy," J. Biomed Opt., vol. 19, No. 6, p. 067003, Jun. 2014,doi: 10.1117/1.JBO.19.6.067003.

Moor, K., et al., "Study of virus by Raman spectroscopy," Proc. SPIE, Imaging, Manipulation, and Analysis of Biomolecules, Cells, and Tissues XI, vol. 8587, 85871X (Feb. 22, 2013); https://doi.org/10.1117/12.2004476.

Nguyen, A. H., et al.,"Bioanalytical applications of surface-enhanced Raman spectroscopy: de novo molecular identification," Rev. Anal. Chem., vol. 36, No. 4, Dec. 2017, pp. 20160037. https://doi.org/10.1515/revac-2016-0037.

Ramoji, A., et al., "Raman Spectroscopy Follows Time-Dependent Changes in T Lymphocytes Isolated from Spleen of Endotoxemic Mice," ImmunoHorizons, vol. 3, No. 2, pp. 45-60, Feb. 1, 2019, DOI: https://doi.org/10.4049/immunohorizons.1800059.

Rau, J.V., et al., "Proof-of-concept Raman sepctroscopy study aimed to differentiate thyroid follicular patterned lesions," Scientific Reports, vol. 7, p. 14970, Nov. 2, 2017, https://doi.org/10.1038/s41598-017-14872-1.

Smith, Z.J., et al., "Raman Scattering in Pathology," Analytical Cellular Pathology , vol. 35, pp. 145-163, Jan. 2012, IOS Press.

Willner, M., et al.,"Quantitative Three-Dimensional Imaging of Lipid, Protein, and Water Contents via X-Ray Phase-Contrast Tomography," PLOS ONE, vol. 11, No. 3, https://doi.org/10.1371/journal.pone.0151889.

Yeh, Y-T, et al., "A rapid and label-free platform for virus capture and identification from clinical samples," PNAS, vol. 117, No. 2, pp. 895-901, Jan. 14, 2020, https://www.pnas.org/cgi/doi/10.1073/pnas.1910113117.

Yeh, Y-T., et al., "Tunable and label-free virus enrichment for ultrasensitive virus detection using carbon nanotube arrays," Science Advances, vol. 2, No. 10, e1601026, Oct. 7, 2016,DOI: 10.1126/sciadv.1601026, AAAS, Washington, DC.

* cited by examiner

SURFACE ENHANCED RAMAN SPECTROSCOPY POINT OF CARE VIRUS DETECTION SYSTEM

RELATED APPLICATIONS

The present application claims benefit from earlier filed U.S. Provisional Application No. 63/058,180, filed Jul. 29, 2020, which is incorporated by reference in its entirety for all purposes.

BACKGROUND

Field of Invention

A present application is directed to a system and method utilizing Surface Enhanced Raman Spectroscopy (hereinafter "SERS") and an optical slicer high-throughput virtual slit for the detection of pathogens in a point of care device. Pathogens include an infectious micro-organism or agents, such as a virus, bacterium, protozoan, prion, viroid, or fungus, and their related antibodies and epitopes. In particular, the detection of viruses such as SARS-CoV-2 (COVID-19), antibodies, and epitopes is achieved by way of combining SERS and virus capture kits.

Discussion of the Related Art

The four technical criteria needed for accurate pathogen analysis with Raman spectroscopy are:

1. High speed of analysis over a large spatial area where pathogens are deposited over the entire large spatial area. Large spatial area refers to areas greater than 100 micron squared, 2. High spectral resolution simultaneous with high sensitivity across a large spectral range in a large spatial area of sample analytes where target microbes are distributed, 3. Detection of a large wavelength region of Raman scatter across a large spatial area of a sample assuring the spectral features of the pathogens are displayed to allow for accurate identification and quantification of the target pathogens from interferences, and 4. Ability to get a large spatial area quickly imaged with fast analysis time providing spectral high resolution and high sensitivity of the large sample area without the use of a confocal optical microscope or the mapping of individual cells typically necessary for Raman analysis.

Polymerase Chain Reaction analysis is considered by many to be the benchmark technique but it is slow, requires viral growth to compensate for low sensitivity, electricity to heat cycle for growth, numerous reagents and high level laboratory training. Additionally, commercially available SERS systems that detect pathogens including viruses are physically large and heavy limiting where they can be deployed.

Confocal microscopes can be and are hyphenated with Raman spectrometers to perform pathogen analysis. In conventional slit controlled Raman systems, the confocal has a first slit to control depth of field and a second slit to pass light into the spectrometer. The first confocal slit limits the spatial range scanned in order to scan through a single cell to get information at depth while the second confocal slit to the Raman spectrometer controls spectral quality. Resolution and sensitivity of the combined system are inversely related.

These slit controlled Raman spectrometers which are attached to a confocal microscope have been modified for Raman excitation transmission. They have inherent problems, and these problems make them unacceptable for viral identification and quantitative applications, even though the large optics slit systems can get spectrum of different microbes. Among other concerns, they are physically large in size, greater than two by three feet in dimension and thus they are difficult to be portable and very hard to use in a point of care location. Additionally, these spectrometers are complex systems with over 50 main components and thousands of subcomponents. This complexity makes them difficult or impossible to use outside of a laboratory setting. Usually, trained operators are required to run and maintain these devices.

Furthermore, the relationship of spectral resolution and sensitivity (intensity of a particular concentration) is inverse for these spectrometers. To achieve high resolution, slits must be closed or very narrow which reduces energy. So large optics and high-powered lasers with expensive optics are used and a Raman microscope is used to focus onto small areas for viral analysis. The microscope are confocal which limits the analysis area to single cells or small areas. The confocal slit limits the spatial size to a small area, and the spectral second slit limits the resolution and sensitivity. This setup leads to analysis times that are long, anywhere from hours to days, in order to map the 100s of points with narrow slits required to obtain the desired resolution.

Variable slit technologies spectrometers have the resolution inversely related to the sensitivity because a physical slit is used to control resolution and inversely the sensitivity. These spectrometers are not imaging devices so in order to visualize and analyze pathogens and look at small areas or single cells an optical microscope is hyphenated.

Variable slit technology spectrometers whose spectral resolution spectrally is inversely related to sensitivity are difficult to use for the biological detection of pathogens, viruses, bacteria, fungus, and microbes, etc. This difficulty arises from the isolation of cells on the microscope which requires high spectral resolution, so the slit must be small which weakens the sensitivity of the Raman scatter. Without high resolution, the spectral features necessary to identify pathogen fingerprints would be difficult to obtain. But when the slits are opened to increase sensitivity, the resolution gets worse obscuring the features needed to get accurate results.

Because the slits need to be open for sensitivity, the collection times are long because they cannot be so open as to provide the highest signal/noise ratio. The analysis time is very long, many hours to days. Adding to the complication of conventional Raman bacterial systems is the hyphenation of an optical microscope used and modified to send Raman scatter to a Raman spectrometer. The hyphenated systems are a visible confocal microscope attached to a Raman spectrometer. The confocal second aperture or slit is needed to obtain a depth profile of a cell but also limits the size of the spatial visible area that can be looked at, generally 100 microns or less. They isolate single cells and analyze them. To map large areas, the stage must be moved, and the new 100 micron area must be analyzed again, thus the time of analysis becomes many hours or days.

Another approach utilized is the use of filters to capture only specific regions of Raman scatter while also providing high sensitivity. These filter instruments are very susceptible to interferences which can make the results less accurate. Typical filters yield a spectral fingerprint which contains only 39 to 40 percent of the spectral lines. These filter systems provide incomplete spectral fingerprint data which can preclude detection of other contaminants in the sample. Intensive AI or other mathematical filtering is used to try and make identification with poor data. These systems limit the spectral frequency range of analysis to get higher sensitivities in a certain range. This compromise creates extremely poor accuracy results for microbes. To accurately identify and quantitate the fine Raman features of a pathogen or microbe, a wide range of wavelengths from 3030 $cm^{-1}$ to 33333 $cm^{-1}$ needs to be used.

Clearly, there is a need for a rapid, accurate, and inexpensive method and system for detection of various pathogens including the virus responsible for causing COVID.

SUMMARY OF THE DISCLOSURE

The present disclosure is directed to a method of detecting analytes by exciting an input area with radiation to produce an input beam, reformatting, with an optical slicer system, the input beam to produce an output beam, dispersing the output beam to produce an output area, capturing excitation data from the output area, and determining, with a processor, a presence of a particular analyte in the input area based on the excitation data. The input area can be greater than 100 micron squared and less than one million microns squared.

Also disclosed is a method for detecting analytes, the method including exciting an input area with radiation to produce an input beam, reformatting, with an optical system, the input beam to produce an output beam, dispersing the output beam to produce an output area, capturing excitation data from the output area with a spectral detector, wherein the output beam forms the output area on the spectral detector, determining, with a processor, a presence of a particular analyte in the input area based on the excitation data, and having the input area greater than 100 micron squared and less than one million microns squared.

According to various embodiments of the presently disclosed method, the reformatting maintains spectral characteristics of the input area. Reformatting also maintains or enlarges spatial dimensions of the input area. The output beam consists of light waves ranging from 3030 $cm^{-1}$ to 33333 $cm^{-1}$ (300 to 3300 nm) which disperses to the output area. The output area is then pixelated into pixels to capture the excitation data, and the presence of analyte is determined by comparing the excitation data from one or more of the pixels to a spectral fingerprint, and calculating a probability of the presence of the analyte.

Additionally disclosed is a system to detect analytes, the system including a radiation source to excite an input area with radiation to produce an input beam, an optical slicer to reformat the input beam to produce an output beam, a disperser to disperse the output beam to produce an output area, a detector to capture excitation data from the output area, and a processor to determine a presence of a particular analyte in the input area based on the excitation data with the input area being greater than 100 micron squared and less than one million microns squared.

A system and method to provide Surface Enhanced Raman Spectroscopy (hereinafter "SERS") using an optical slicer high-throughput virtual slit ("HTVS") for the detection of pathogens in a point of care device is just one embodiment of the teachings of the present disclosure. Pathogens including infectious micro-organism or agents, such as a virus, bacterium, protozoan, prion, viroid, or fungus, and their related antibodies and epitopes. In particular, the detection of viruses such as SARS-CoV-2 (COVID-19), antibodies, and epitopes is achieved by way of combining SERS with the optical slicer system and virus capture kits.

In order to achieve a small form factor with high diagnostic accuracy for point of care system for use in emergency, triage or clinical care, offices, businesses, schools, ports of entry, homes, etc. a high-throughput virtual slit coupled with a SERS detector was employed. The HTVS optical slicer system provides better resolution for the identification of analytes, and simultaneously higher sensitivity as compared to other SERS systems. Various embodiments of the presently disclosed system allow for the development of a point of care device that can be in a small form factor including portable versions.

The presently disclosed instrument in combination with a pathogen capture kit can detect multiple viruses, antibodies/antigens from, for example, saliva, blood, and nasal swab specimens. Rapid definitive detection of numerous pathogens, including SARS-CoV-2 (COVID-19) can be achieved in tens of seconds rather than tens of hours. There is no need to grow any viruses, and very few to no reagents are required. Various embodiments of the presently disclosed device require no more than very simple laboratory training or can be utilized in a home testing environment.

Additional features will be set forth in the description that follows, and in part will be apparent from the description, or may be learned by practice of what is described.

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

In order to describe the manner in which the above-recited and other advantages and features may be obtained, a more particular description is provided below and will be rendered by reference to specific embodiments thereof which are illustrated in the appended drawings. Understanding that these drawings depict only typical embodiments and are not, therefore, to be limiting of its scope, implementations will be described and explained with additional specificity and detail with the accompanying drawings.

Throughout the drawings and the detailed description, unless otherwise described, the same drawing reference numerals will be understood to refer to the same elements, features, and structures. The relative size and depiction of these elements may be exaggerated for clarity, illustration, and convenience. In the drawings.

DETAILED DESCRIPTION

The present teachings may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

According to several embodiments of the presently disclosed method, analytes can be detected by the method including exciting an input area with radiation to produce an input beam, reformatting, with an optical slicer system, the input beam to produce an output beam, dispersing the output beam to produce an output area, capturing excitation data from the output area, and determining, with a processor, a presence of a particular analyte in the input area based on the excitation data; with the input area being greater than 100 micron squared and less than one million microns squared.

The radiation can excite the input area which can contain a sample and produce molecular vibrations creating scattered light which creates the input beam. These molecular vibrations can be in the Raman portion of the spectrum. Also in this method, the reformatting maintains spectral characteristics of the input area, and also maintains or enlarges spatial dimensions of the input area. The output beam can consist of light waves ranging from 3030 $cm^{-1}$ to 33333 $cm^{-1}$, in other words, in the Raman spectra range.

The capturing comprises pixelating into pixels the output area to capture the excitation data, and the captured excitation data provides a spectral resolution of less than 5 $cm^{-1}$.

Using the presently disclosed method, the presence of hot spots, and the identification of a particular analyte concentration can be determined. The determining can be accomplished by comparing the excitation data from one or more of the pixels to a reference spectral fingerprint and calculating a probability of the presence. The determining can further include averaging the excitation data from one or more of the pixels, comparing the averaged excitation data to a spectral fingerprint, and calculating a probability of the presence. The spectral fingerprint can be a Raman spectra pattern received from a library, which can be accessed remotely, or can be stored internally.

For highly contagious pathogens the time from sample collection to determination of whether a pathogen of interest is present or not is of high interest, and the presently disclosed method can perform the exciting of scattered light, the reformatting, the dispersing, and the capturing together in less than 10 seconds and in some embodiments, the method can have the exciting, the reformatting, the dispersing and the capturing together performed in less than 3600 seconds. The time to completion can range from less than 10 seconds, from less than 60 seconds, from less than 120 seconds, from less than 180 seconds, from less than 240 seconds, less than 300 seconds, to less than 3600 seconds. The time required to complete the process will depend on numerous factors including, for example, the method of sample capture, sample preparation, concentration of analyte in the sample, the sensitivity of the detector, processing power of the processor performing the data collected, and the power of the radiation source.

According to various embodiments of the presently taught method, the method can further include positioning a detector, in many cases, comprising a Raman detector, and the output beam forms the output area on the detector.

The presently disclosed method can have a sample positioned in the input area, and the sample can contain analytes comprising one or more member selected from virus, bacterium, protozoan, prion, viroid, fungus, their related antibodies and epitopes, or a combination thereof, of particular interest are COVID-19 viruses.

A device or system to detect analytes is also disclosed in the present application, the system includes a radiation source to excite an input area with radiation to produce an input beam, an optical slicer system to reformat the input beam to produce an output beam, a disperser to disperse the output beam to produce an output area, a detector to capture excitation data from the output area, and a processor to determine a presence of a particular analyte in the input area based on the excitation data with the above-mentioned input area having an area greater than 100 micron squared and less than one million microns squared. The input beam produced by the radiation can include the Raman spectra of the analyte.

The presently taught Raman system and method can provide spectral imaging and spectral fingerprints (spectra) without the use of a hyphenated microscope coupled to the SERS spectrometer. The present system avoids the limitations of physical slit controlled spectrometers and a hyphenated optically modified microscope to gather scatter over a small area and the limitations of filters to analyze pathogens over a large area.

With the optical slicer system or HTVS as utilized in the presently disclosed method and systems, there is no compromise between resolution and sensitivity. Both variables are high with the high throughput system simultaneously and quickly provide data with high sensitivity over a large frequency range which enables the visualization of even the smallest spectral features. This visualization leads to identifying pathogen targets or interferences within the sample material matrix.

The method's high sensitivity allows for fast analysis with no need to move from point to point across the sample area, or to image the pathogens themselves. The present method also provides for large area imaging and spectral data creation simultaneously.

Conventional Raman spectrometers exhibit an inverse relationship between resolution and sensitivity that does not exist in the presently disclosed optical slicer system. The presently disclosed virtual slit, versus the physical slit, allows almost 99% of the energy to be brought from the scatter to the detector at high fidelity, that is both resolution and sensitivity. In conventional physical slit Raman spectrometers dispersing the beam of scattered light from the sample disperses the existing low energy by the physical slits being closed or have low resolution with open slits. So, to compensate the energy is reduced and inversely the sensitivity even if light spots are spread into lines. This process degrades accuracy by reducing important spectral features or adds stray light thus decreasing accuracy of spectral features and increasing analysis time above 3600 seconds.

The presently disclosed HTVS virtual slit method and system can use Raman technology which can provide the capability to identify large areas containing viruses and to identify and quantitate the virus. The optical slicer system can be used for large imaging of small spectral features in a large area. The technology avoids the inverse relationship between resolution and sensitivity that is observed with different slit spectrometer and filter systems. The presently disclosed optical slicer system provides a high spectral resolution over a large spectral area with high sensitivity across the entire spectral range.

The presently disclosed optical slicer system has a direct relationship with both high resolution and sensitivity, that does not require slit narrowing. This high sensitivity allows for low viral load detection across a large spatial area when applied to viruses with SERS. The presently disclosed optical slicer system has integral imaging capability over a large area with high resolution and sensitivity without the need for microscopes and small area analysis which allows for sensitive and highly resolved large sample area detection of viruses.

The present application describes the use of the optical slicer system to analyze large areas greater than 100 microns large areas to identify and quantitate viruses quickly with high accuracy without a microscope to analyze pathogens and other microbes. This advantage is derived from the imaging and spectral data from Raman scatter are integral parts of the function and design of the HTVS optical slicer system. For virus analysis, conventional slit and filter spectrometers and conventional methods use a microscopic visualization with a Raman microscope which passes to the Raman spectrometer and is generated from small areas <100 microns to visualize small areas or <10 microns for individual cells. They can scan or use arrays, but all these methods violate the four conditions needed to provide fast and accurate identification of viruses. The presently disclosed system can image the input area containing the sample without an optical microscope and confocal capability. HTVS optical slicer system does large area analysis over a broad spectral range without the need for hundreds of points of analysis and stitching the data together. This multiple point mapping takes a long time unlike HTVS's large area imaging and spectral analysis.

Figure 1A:
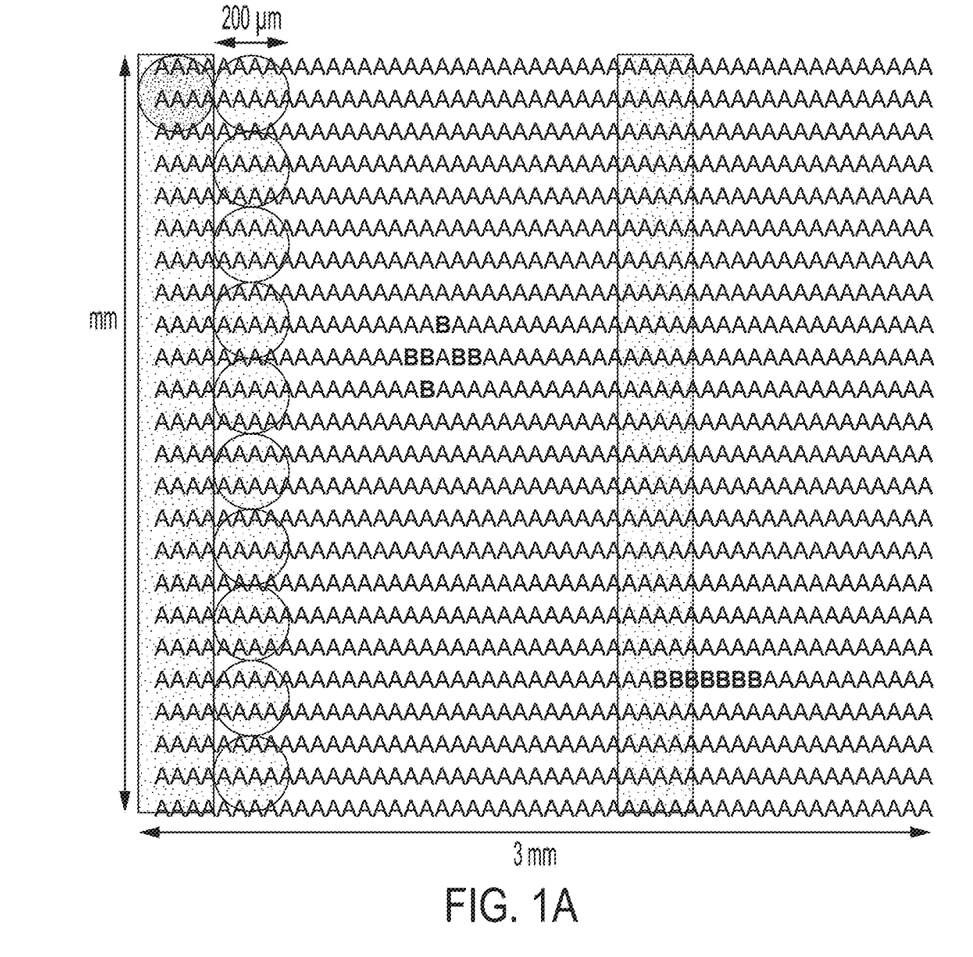
FIG. 1 is a drawing of the line scanning method according to one embodiment of the present disclosure.
Figure 1B:
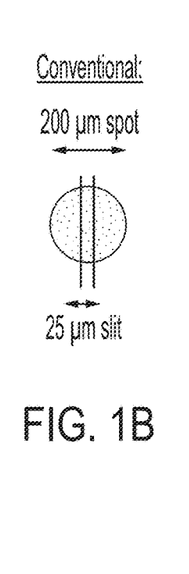
Figure 1C:
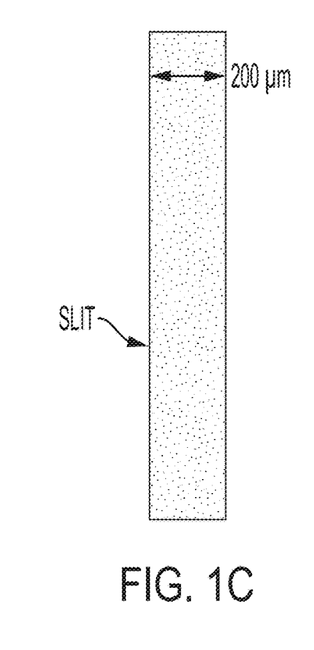

FIG. 1 illustrates the one embodiment of the present method with a comparison of the effectiveness of line scanning with the presently disclosed virtual slit versus point scanning with conventional Raman spectrometers. Utilizing the presently disclosed optical slicer or HTVS system provides for large scale simultaneous acquisition of signal from the sample area as set forth in FIG. 1A. In this specific embodiment the virtual slit of the present disclosure is 200 μm by 3 mm as illustrated in FIG. 1C, and is compared to conventional spot set forth in FIG. 1B having a radius of 200 μm. With the following parameters for the point and the slit scanning the same sample area:

Point: Point Scanning: 200 μm laser spot
Scan Time: 225 frames
Laser Intensity: 100 mW/0.03 mm$^2$=3.2 W/mm$^2$
Slit: Line Scanning: 200×3 mm laser line
Scan Time: 15 frames
Laser Intensity: 600 mW/0.06 mm$^2$=1.0 W/mm$^2$ In this example, there is a loss of a factor of 3.2 in the power density, there is a gain of a factor of 15 in scan time to scan the entire sample area, but with the light throughput of the laser spot being only 16% of the larger HTVS slit, the presently disclosed method has a net 23× gain in scan time.

The dimensions of the HTVS slit can vary as needed of each application. In some embodiments, it can be 3 mm by 0.1 mm, and in any case can have an area larger by a factor of 30 compared to conventional pinhole designs.

The HTVS system described herein can utilize an optical slicer system to manipulate the input beam. The optical slicer system can include a beam compressor, a beam reformatter, and a beam expander to produce an output beam. In some embodiments of the presently disclosed optical slicer system, the output beam can produce an output spot that is expanded in a first dimension and compressed in a second dimension relative to the input beam. One example of a suitable optical slicer system is described in U.S. Pat. No. 8,384,896 B2 to Meade et al., the entire disclosure of which is incorporated herein for all purposes.

Figure 3:
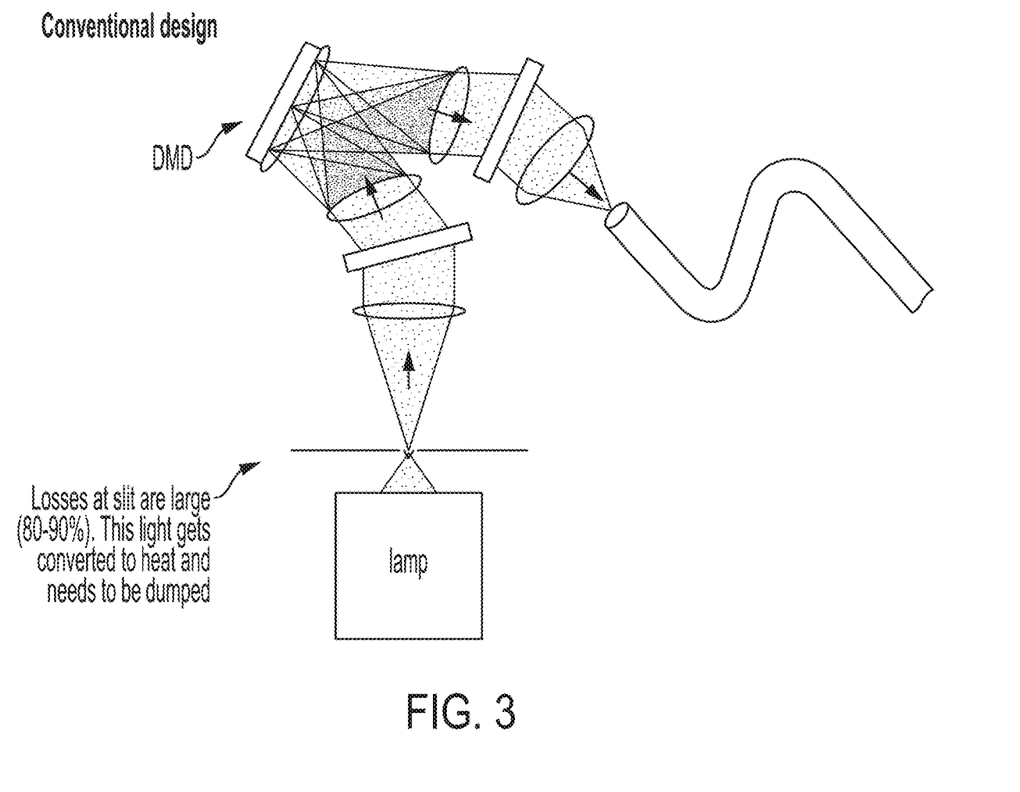
FIG. 3 is a general plan schematic of a known conventional system.
Figure 4:
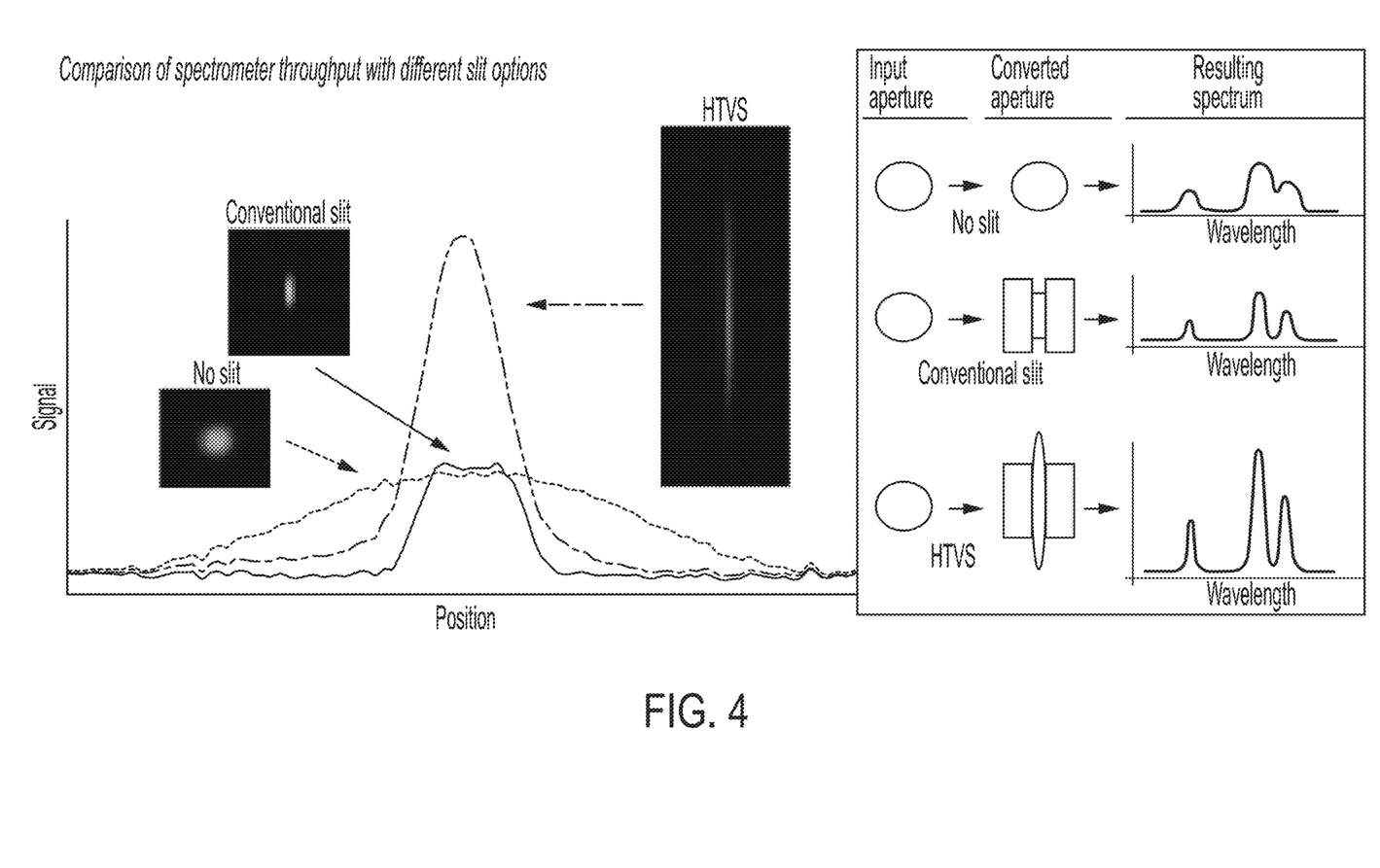
FIG. 4 is a comparison of light throughput according to one embodiment of the present disclosure.

The advantages of the presently disclosed system are clearly shown in FIG. 4 where the spectrum from the presently disclosed system is compared to two known systems. In FIG. 4, the three systems are an unmodified input beam or aperture, a conventional slit where the input beam is passed through a simple restrictive slit, and the presently disclosed system that modifies the beam in two dimensions to increase light throughput without loss of resolution. The resulting spectrum illustrate the significant advantages of the present system with high throughput and resolution of signal simultaneously. The conventional designed system is illustrated in FIG. 3 with the losses of light at the conventional slit highlighted. The light loss at the slit can be in the range of 80 to 90% and is lost as waste heat. This heat needs to be handled by the system and can result in large heat handling systems such as heat sinks and fans.

Figure 2:
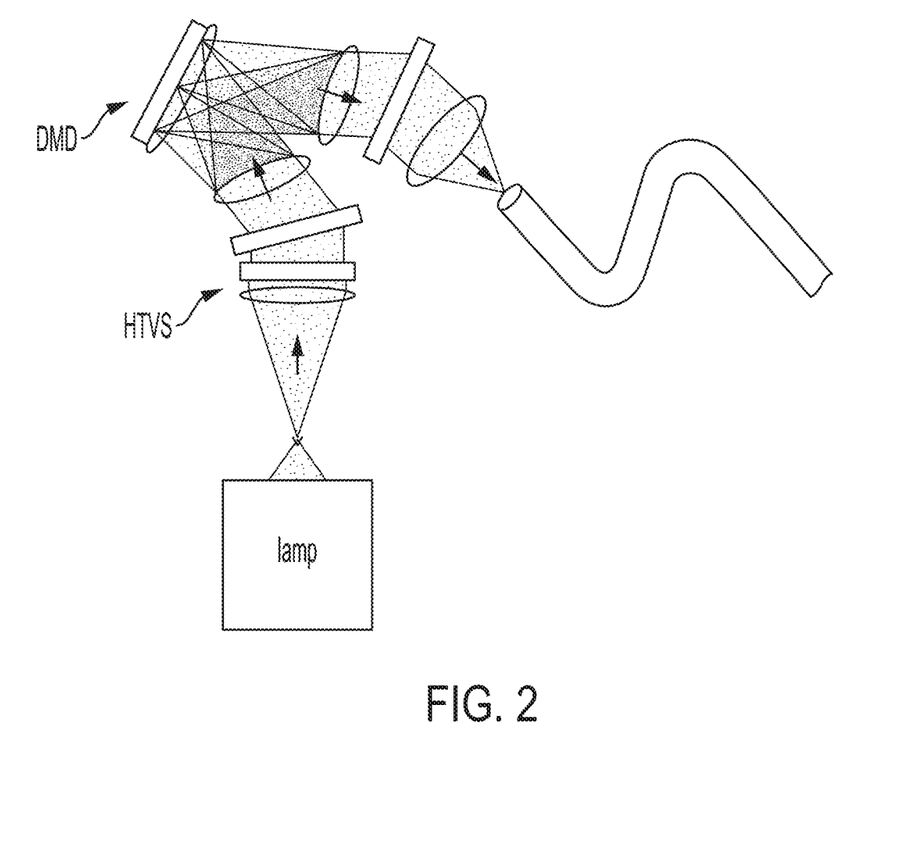
FIG. 2 is a general plan schematic according to one embodiment of the present disclosure.

One embodiment of the presently disclosed system is illustrated in FIG. 2, with the optical slicer system or HTVS positioned after the lamp source.

Figures 5A, 5C:
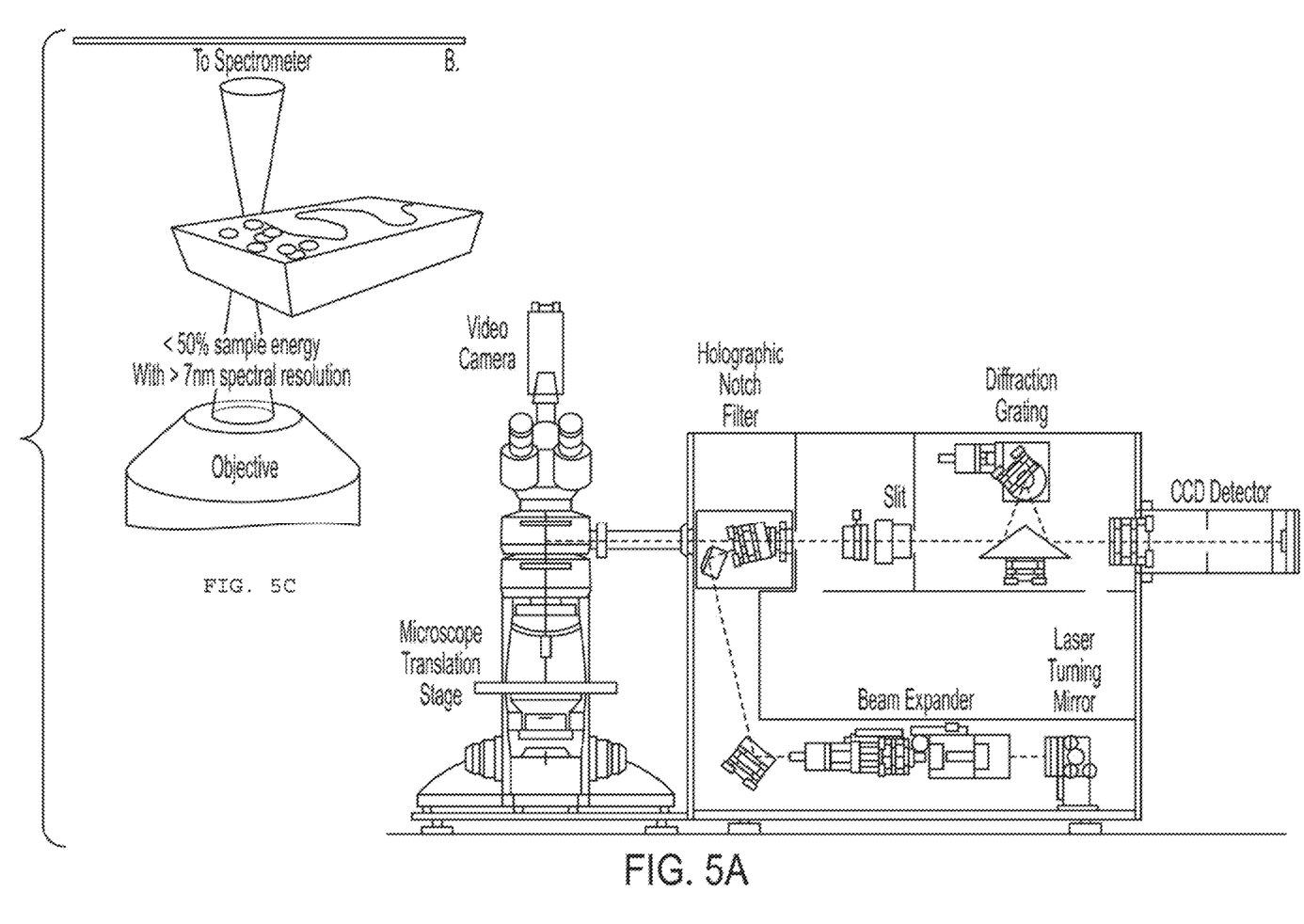
FIGS. 5A, 5B, 5C and 5D are graphic comparisons of a confocal slit spectrometer and one embodiment of the present disclosure.
Figure 5B:
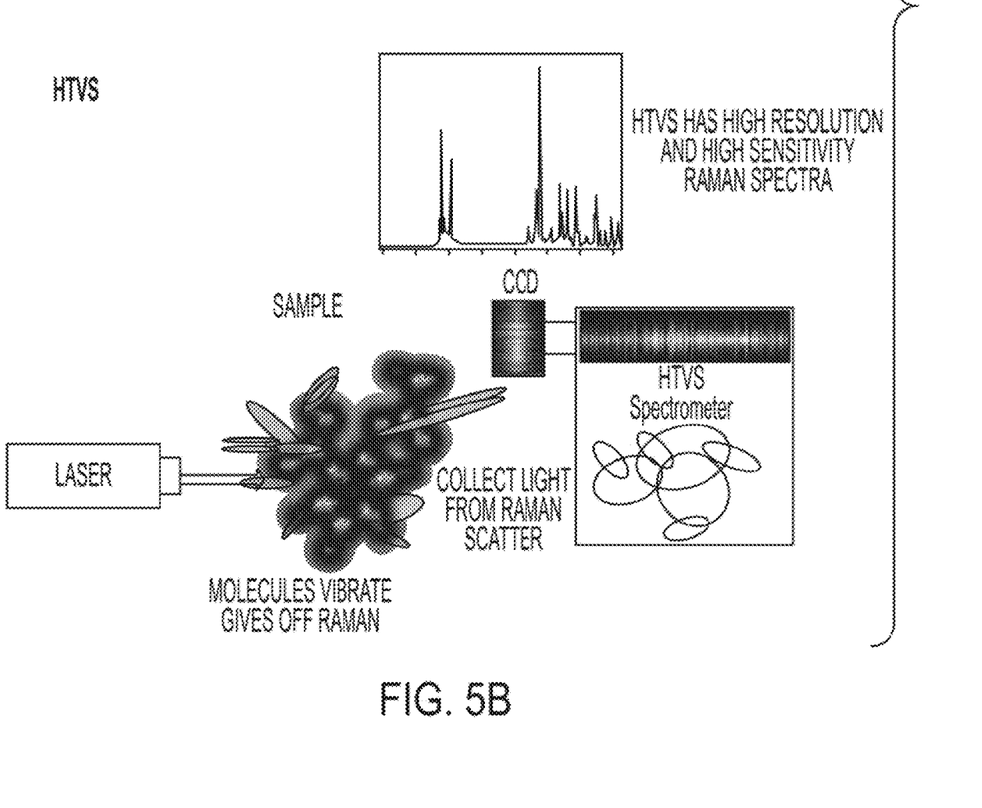
Figure 5D:
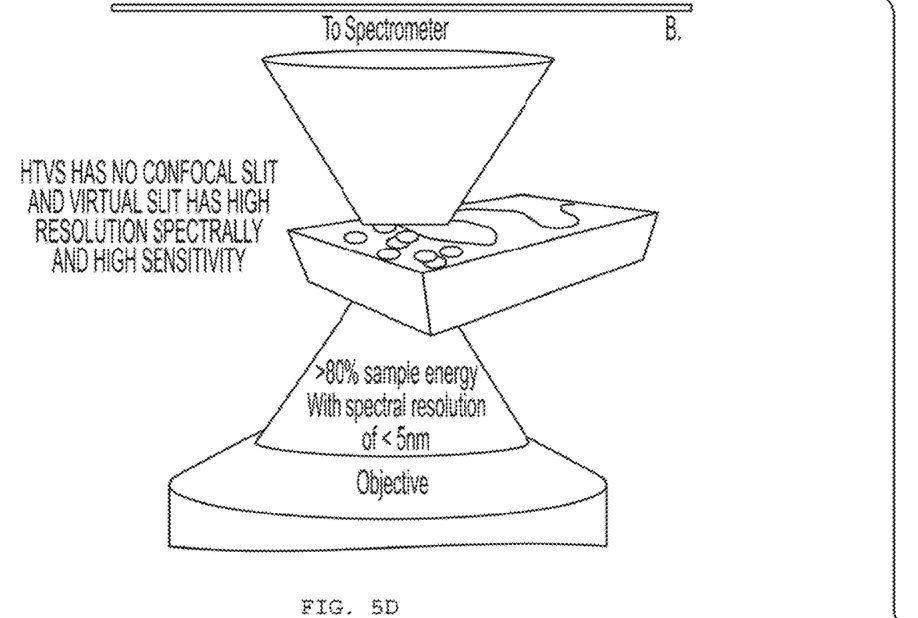

FIGS. 5A-D present a comparison of the one embodiment of the present disclosure to a conventional slit spectrometer. In order to being able to analyze microbes and pathogens, the spectral resolution of a spectrometer must be 0.1 of the natural bandpass of an analyte to resolve close spectral features. Thus, a 1 nm spectral bandpass can resolve natural features of 10 nm. In a conventional system, as shown in FIGS. 5A and 5C, narrowing the slit to 1 nm spectral resolution to achieve resolution of 10 nm features the energy will be reduce by greater than 50%. As shown in FIGS. 5A and 5C, the small slit has low sensitivity and small spatial area so it must find cells and stitch signal together. The light reformatting process by the presently disclosed virtual slit, as shown in FIGS. 5B and 5D, can maintain 98% of the energy with a spectral bandpass at 1 nm so fine features can be resolved and high sensitivity maintained. The presently disclosed system can see the entire sample filed and differentiate the target signal; there is no need to find every cell or stitch spatial spectra.

The presently disclosed method for pathogen detection can be applied in the detection of SARS-CoV-2 and other viruses individually or in a combinatory mixture such as saliva or blood.

The presently disclosed system or instrument can be applied to other pathogens in human biofluids, as well as on many products such as food, boxes, packaging, money, and in the air. Additional applications include diagnosis, vaccine development, presence and surface detection, and the triage of humans, animals, and objects for the presence of viruses. These devices can be utilized in numerous locations including medical facilities, urgent care, laboratories, government (NIH-CDC, DOD, NASA, etc.), schools, business, and ports of call, such as airports and seaports.

The presently disclosed system can achieve the sensitivity and selectivity necessary to detect pathogens such as virus or an abundance of viruses such as those found in saliva or blood. In order to capture the analytes of interest such as viruses, kits employing a combination of separation features such as microfluidics for the purposes of concentrating the virus can be utilized. For greater selectivity, metal-containing particles can be utilized as SERS substrates and capture molecules to provide even greater selectivity. In some instances, particles, nanotubes, and nanoparticles containing various metals including gold, silver, aluminum, and combinations provide greater selectivity.

In some embodiments, capture molecules designed for specific analytes of interest can be positioned on the SERS substrate to further enhance the selectivity of the detection method.

Figure 6:
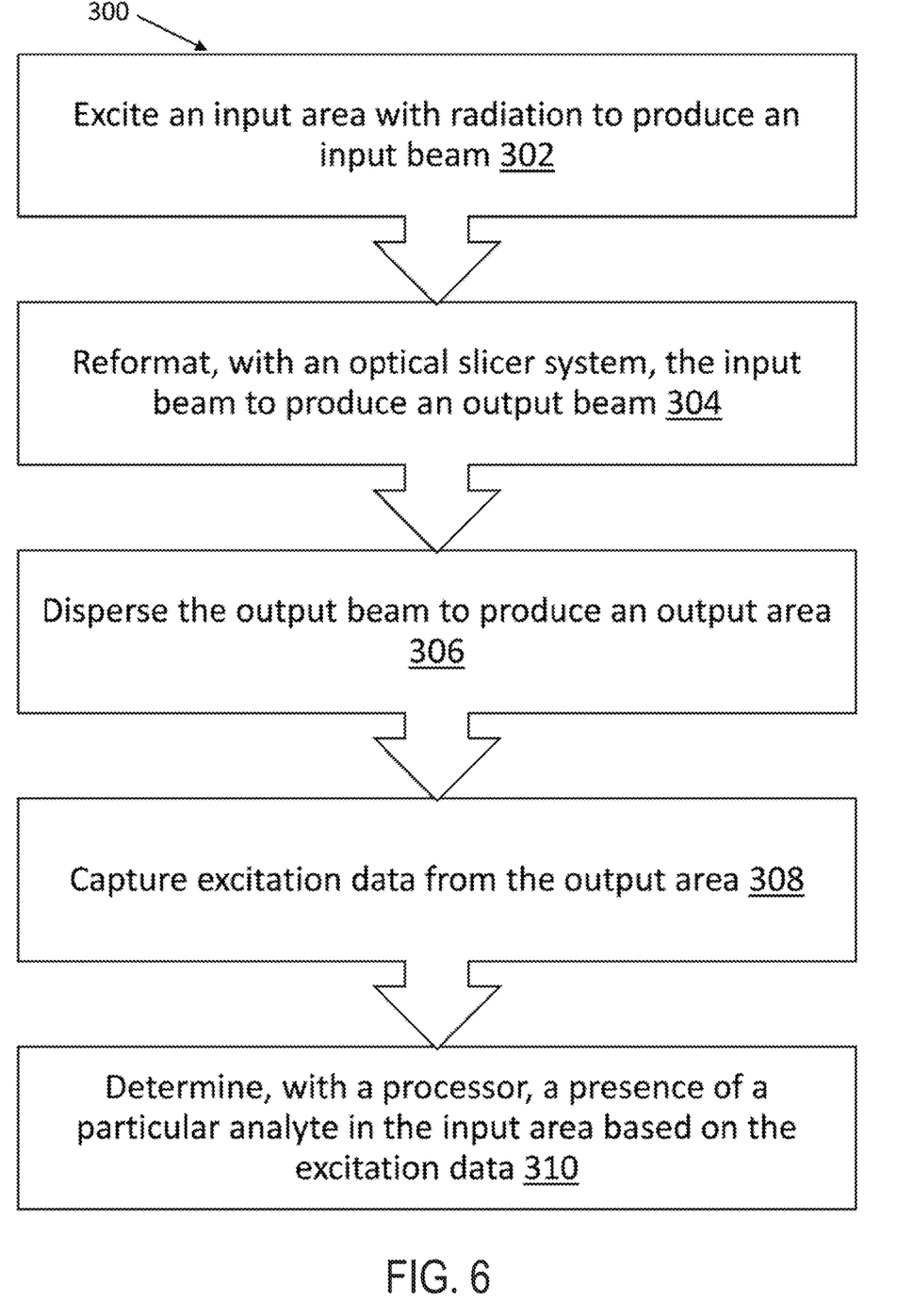
FIG. 6 illustrates a method for detecting analytes according to various embodiments.

FIG. 6 illustrates a method for detecting analytes according to various embodiments.

A method 300 for detecting analytes may include an operation 302 to excite an input area with radiation to produce an input beam. The method 300 may include an operation 304 to reformat, with an optical slicer system, the input beam to produce an output beam. The method 300 may include an operation 306 to disperse the output beam to produce an output area. The method 300 may include an operation 308 to capture excitation data from the output area. The method 300 may include an operation 310 to determine, with a processor, a presence of a particular analyte in the input area based on the excitation data.

Embodiments are discussed in detail throughout. While specific implementations are discussed, this is done for illustration purposes only. A person skilled in the relevant art will recognize that other components and configurations may be used without parting from the spirit and scope of the subject matter of this disclosure.

The terminology used herein is for describing embodiments only and is not intended to be limiting of the present disclosure. As used herein, the singular forms "a," "an" and "the" are intended to include the plural forms as well, unless the context clearly indicates otherwise. Furthermore, the use of the terms "a," "an," etc. does not denote a limitation of quantity but rather denotes the presence of at least one of the referenced items. The use of the terms "first," "second," and the like does not imply any order, but they are included to either identify individual elements or to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Although some features may be described with respect to individual exemplary embodiments, aspects need not be limited thereto such that features from one or more exemplary embodiments may be combinable with other features from one or more exemplary embodiments.

All publications, articles, papers, patents, patent publications, and other references cited herein are hereby incorporated by reference herein in their entireties for all purposes.

Although the foregoing description is directed to the preferred embodiments of the present teachings, it is noted that other variations and modifications will be apparent to those skilled in the art, and which may be made without departing from the spirit or scope of the present teachings.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described in order to best explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

What we claim is:

1. A method for detecting analytes, the method comprising:
   exciting an input area with radiation to produce an input beam;
   reformatting, with an optical slicer system, the input beam to produce an output beam;
   dispersing the output beam to produce an output area;
   capturing excitation data from the output area; and
   determining, with a processor, a presence of a particular analyte in the input area based on the excitation data, wherein the input area is greater than 100 micron squared and less than one million microns squared, and
   reformatting maintains 98% of the energy of the input beam with a spectral bandpass at 1 nm.

2. A method for detecting analytes, the method comprising:
   exciting an input target area with radiation to produce scattered light forming an input beam;
   reformatting, with an optical slicer system, the input beam to produce an output beam;
   dispersing the output beam to produce an output area;
   capturing excitation data from the output area with a Raman detector, wherein the output beam forms the output area on the Raman detector;
   determining, with a processor, a presence of a particular analyte in the input area based on the excitation data, wherein the input area is greater than 100 micron squared and less than one million microns squared,
   the reformatting maintains spectral characteristics of the input area,
   the output beam consists of light waves ranging from 3030 $cm^{-1}$ to 33333 $cm^{-1}$,
   reformatting maintains or enlarges spatial dimensions of the input area,
   the capturing comprises pixelating into pixels the output area to capture the excitation data, and
   the determining comprises comparing the excitation data from one or more of the pixels to a spectral fingerprint, and calculating a probability of the presence.

3. A system to detect analytes, the system comprising:
   a radiation source to excite an input area with radiation to produce an input beam;
   an optical slicer system to reformat the input beam to produce an output beam;
   a disperser to disperse the output beam to produce an output area;
   a detector to capture excitation data from the output area; and
   a processor to determine a presence of a particular analyte in the input area based on the excitation data,
      wherein the input area is greater than 100 micron squared and less than one million microns squared, and the optical slicer system maintains or enlarges spatial dimensions of the input area during reformatting.

4. The system according to claim 3, wherein the input beam comprises the Raman spectra of the analyte.

5. A method for detecting analytes, the method comprising:
   exciting an input area with radiation to produce an input beam;
   reformatting, with an optical slicer system, the input beam to produce an output beam;
   dispersing the output beam to produce an output area;
   capturing excitation data from the output area; and
   determining, with a processor, a presence of a particular analyte in the input area based on the excitation data,
   wherein the input area is greater than 100 micron squared and less than one million microns squared, and
   wherein the output beam consists of light waves ranging from 3030 $cm^{-1}$ to 33333 $cm^{-1}$.

6. The method according to claim 5, wherein the reformatting maintains spectral characteristics of the input area.

7. The method according to claim 5, wherein the excitation data has a spectral resolution of less than 5 cm-1.

8. The method according to claim 5, wherein the reformatting maintains or enlarges spatial dimensions of the input area.

9. The method according to claim 5, wherein the determining identifies a presence of hot spots.

10. The method according to claim 5, wherein the determining identifies a concentration of the particular analyte.

11. The method according to claim 5, wherein the capturing comprises pixelating into pixels the output area to capture the excitation data.

12. The method according to claim 11, wherein the determining comprises
comparing the excitation data from one or more of the pixels to a spectral fingerprint, and
calculating a probability of the presence.

13. The method according to claim 12, wherein the spectral fingerprint comprises a Raman spectra pattern received from a library.

14. The method according to claim 11, wherein the determining comprises
averaging the excitation data from one or more of the pixels,
comparing the averaged excitation data to a spectral fingerprint, and
calculating a probability of the presence.

15. The method according to claim 5, wherein the exciting, the reformatting, the dispersing and the capturing together are performed in less than 10 seconds.

16. The method according to claim 5, wherein the exciting, the reformatting, the dispersing and the capturing together are performed in less than 3600 seconds.

17. The method according to claim 5, further comprising positioning a detector comprising a Raman detector, wherein the output beam forms the output area on the detector.

18. The method according to claim 5, further comprising positioning a sample in the input area, wherein the sample comprises analytes comprising one or more member selected from virus, bacterium, protozoan, prion, viroid, fungus, their related antibodies and epitopes, or a combination thereof.

19. The method according to claim 18, wherein the analytes comprising COVID-19 viruses.

* * * * *